United States Patent
Tomitaka et al.

[11] Patent Number: 6,143,925
[45] Date of Patent: Nov. 7, 2000

[54] PROCESS FOR PRODUCING AROMATIC CARBOXYLIC ACID

[75] Inventors: Tadashi Tomitaka; Michio Umeda, both of Ohtake; Hideaki Iwata, Chiba; Fujimasa Nakao, Ohtake, all of Japan

[73] Assignee: Mitsui Chemicals, Inc., Tokyo, Japan

[21] Appl. No.: 09/325,341

[22] Filed: Jun. 4, 1999

[30] Foreign Application Priority Data

Jun. 5, 1998 [JP] Japan .................................. 10-158039
Aug. 24, 1998 [JP] Japan .................................. 10-237710

[51] Int. Cl.$^7$ .................................................. C07C 51/16
[52] U.S. Cl. ........................................... 562/412; 562/409
[58] Field of Search ...................................... 562/409, 412

[56] References Cited

FOREIGN PATENT DOCUMENTS

| | | |
|---|---|---|
| 54-14098 | 6/1979 | Japan . |
| 4-169551 | 6/1992 | Japan . |
| 5-213816 | 8/1993 | Japan . |
| 6-279353 | 10/1994 | Japan . |
| 8-155265 | 6/1996 | Japan . |
| 1373230 | 11/1974 | United Kingdom . |
| WO96 11899 | 4/1996 | WIPO . |
| WO96 39595 | 12/1996 | WIPO . |
| WO97 27168 | 7/1997 | WIPO . |

*Primary Examiner*—Paul J. Killos
*Attorney, Agent, or Firm*—Birch, Stewart, Kolasch & Birch, LLP.

[57] ABSTRACT

A process for producing aromatic carboxylic acids efficiently by operating a distillation column for separating the vaporized reaction solvent and other useful ingredients from an oxidation reactor while permitting efficient energy recovery without causing any obstruction to turbine and without causing any clogging of the distillation column, said process comprising oxidizing an alkyl aromatic compound in a liquid reaction solvent comprising an aliphatic carboxylic acid with a molecular oxygen-containing gas in the presence of an oxidation catalyst in the said oxidation reactor to form an aromatic carboxylic acid, guiding the oxidation reactor exhaust gas into the distillation column to subject it to a distillation, passing the distilltion overhead gas to a condenser to form a condensate, which is returned to the distillation column, and to generate a steam on the shell side, which is guided to a steam turbine for energy recovery, and burning the condenser exit gas in order to drive a gas turbine for energy reclamation.

11 Claims, 2 Drawing Sheets

PROCESS FOR PRODUCING AROMATIC CARBOXYLIC ACID

FIELD OF THE INVENTION

The present invention relates to a process for producing an aromatic carboxylic acid by a liquid phase oxidation of an alkyl aromatic compound having substituent alkyl groups or partially oxidized alkyl group(s) with a molecular oxygen-contaning gas.

BACKGROUND OF THE INVENTION

Aromatic carboxylic acids are important as fundamental chemical product and, in particular, aromatic dicarboxylic acids are useful for the starting material of fibers, resins and the like. For example, terephthalic acid has found its growing demand as the starting material for polyester fiber in recent years.

A process has hitherto been employed in general for producing an aromatic carboxylic acid, in which an aromatic compound having substituent alkyl group(s) is subjected to a liquid phase oxidation by bringing it into contact with a molecular oxygen-containing gas in a liquid reaction solvent comprising a lower aliphatic carboxylic acid, such as acetic acid, in the presence of an oxidation catalyst composed of heavy metal compound(s) and of bromine compound(s) in an oxidation reactor. According to such a production process, a mixture composed of an alkyl-substituted aromatic compound, such as paraxylene, as the starting material, acetic acid as the reaction solvent and a catalyst is supplied to the oxidation reactor while introducing thereinto a molecular oxigen-containing gas, such as air, to cause oxidation, whereby an aromatic carboxylic acid, such as terephthalic acid is obtained.

The exhaust gas from the oxidation reactor contains a vaporized portion of the reaction solvent and an entrained, or carried-over, portion of liquid droplets of the reaction mixture containing the catalyst. In order to recover and reuse them, a technique has been proposed, in which a distillation column is arranged so as to communicate to the top of the oxidation reactor and the distillation is carried out under utilization of the heat content of the oxidation exhaust gas so as to recover and reflux the solvent and catalyst to the oxidation reactor (See, for example, Japanese Patent publication Sho-54-14098 B and Japanese Patent Application Kokai Hei-6-279353 A). In this process, the distillation overhead gas is cooled in a condenser by a cooling water to condense steam and the so-condensed water is refluxed to the distillation column.

In order to attain a recovery of energy, it has also been proposed to incorporate in such an apparatus having a distillation column disposed directly above the oxidation reactor a technical measure of heating the distillation column overhead gas or occasionally even further burning it to drive a turbine (expander) (See WO 96/11899 and WO 97/27168). For energy recovery by a turbine, a higher temperature difference is required in general and, therefore, the above-mentioned technique does not employ a condenser subsequent to the distillation colmn so as not to lower the temperature but, on the contrary, employs heating of the overhead gas before it is guided to the turbine for attaining energy recovery.

Here, there occurs a problem that the turbine may be apt to suffer from obstructive phenomena of corrosion and scale formation, since the distillation colomn overhead gas contains, though in small amounts, corrosive ingredients, such as acetic acid etc., and scale-forming components. In addition, it is also problematic in the above-mentioned technique, that the mother liquor separated in the purification step is recycled to the distillation column, wherein the column may tend to suffer from clogging due to accumulation of the remaining carboxylic acid crystals.

On the other hand, there has been proposed a technique in which the exhaust gas from the oxidation reactor is directly guided to a condenser to form a condensate which is subjected to distillation to separate acetic acid, whereupon the so-separated acetic acid is returned to the oxidation reactor, while the condenser exit gas is passed to a layer of activated carbon to collect methyl acetate by adsorption thereon, which is desorbed thereafter by steaming the activated carbon layer and is then hydrolyzed to reproduce acetic acid to be recycled to the oxydation reactor (See Japanese Patent Application Kokai Hei-4-169551 A).

This technique requires, however, separation of each of the components for both the condensate and the condenser exit gas, since the oxidation reactor exhaust gas is subjected directly to condensation in the condenser, in addition to intricate operations for the absorption and desorption of the activated carbon as well as for the hydrolysis of methyl acetate desorbed.

SUMMARY OF THE INVENTION

An object of the present invention is to provide a process for producing an aromatic carboxylic acid which permit to attain an efficient energy recovery with turbine without causing any obstructive influence on the turbine and to attain an efficient production of the aromatic carboxylic acid under incorporation of distillation of the oxidation exhaust gas without suffering from clogging of the distillation column.

Another object of the present invention is to provide a process for producing an aromatic carboxylic acid efficiently with lower energy consumption under recovery of useful ingredients including low boiling aliphatic carboxylic acid esters and under attainment of energy recovery.

Thus, the present invention proposes the followings:

(1) A process for producing aromatic carboxylic acid by a liquid phase oxidation of an alkyl aromatic compound with a molecular oxygen-containing gas under a high temperature/high pressure condition in an oxidation reactor, comprising an oxidation step in which the alkyl aromatic compound is oxidized in a liquid reaction solvent comprising an aliphatic carboxylic acid with the molecular oxygen-containing gas in the oxidation reactor in the presence of an oxidation catalyst to form an aromatic carboxylic acid, a distillation step in which the exhaust gas from the oxidation reactor is guided to a distillation column to subject it to distillation therein and liquid fractions formed therein containing the reaction solvent are returned to the oxdation reactor, a condensing step in which the distillation column overhead gas is cooled in a condenser so as to form a condensate which is returned to the distillation column to generate a steam in the condenser, a burning step in which the condenser exit gas is burnt in a burning chamber and an energy recovering step in which energy is recovered from the heat contents of the steam generated in the condenser and of the combustion gas formed in the burning chamber.

(2) The process according to above (1), comprising further an absorption step in which low boiling esters of the aliphatic carboxylic acid are retained in the gas phase in the condensing step and the condenser exit gas is brought into contact with an absorbing liquid containing an aliphatic carboxylic acid to absorb the aliphatic carboxylic acid esters, whereupon the absorbing liquid which contains the absorbed aliphatic carboxylic acid esters is supplied to the oxidation reactor, while the delivery gas from the absorption step is burnt in the burning chamber.

(3) The process according to the above (1) or (2), comprising further a gas washing step in which the absorption step delivery gas is brought into contact with a washing water to absorb the aliphatic carboxylic acid contained therein.

(4) The process according to either one of the above (1) to (3), in which the temperature of the condenser exit gas is maintained within the range from 50 to 150° C. so as to retain methyl acetate within the exit gas.

(5) The process according to either one of the above (1) to (4), in which energy recovery is effected by means of a steam turbine and a gas turbine.

(6) The process according to either one of the above (1) to (5), in which the molecular oxygen-containing gas is supplied to the oxidation reactor under compression by using the recovered energy.

(7) The process according to either one of the above (1) to (6), in which liquid extraction ports are provided on the distillation column.

(8) The process according to either one of the above (1) to (7), in which a distillate is extracted from the distillation column at a lower portion thereof and this distillate is used as the absorbing liquid.

(9) The process according to either one of the above (1) to (8), in which the distillation column is constructed so as to permit withdrawal of the distillate of the lower portion of the column out to the system outside in emergency.

(10) The process according to either one of the above (1) to (9), in which the condensation step is performed using a plurality of condensers in sequence.

(11) The process according to either one of the above (1) to (10), in which the condenser is a kettle type.

DETAILED DESCRIPTION OF THE INVENTION

Figure 1:
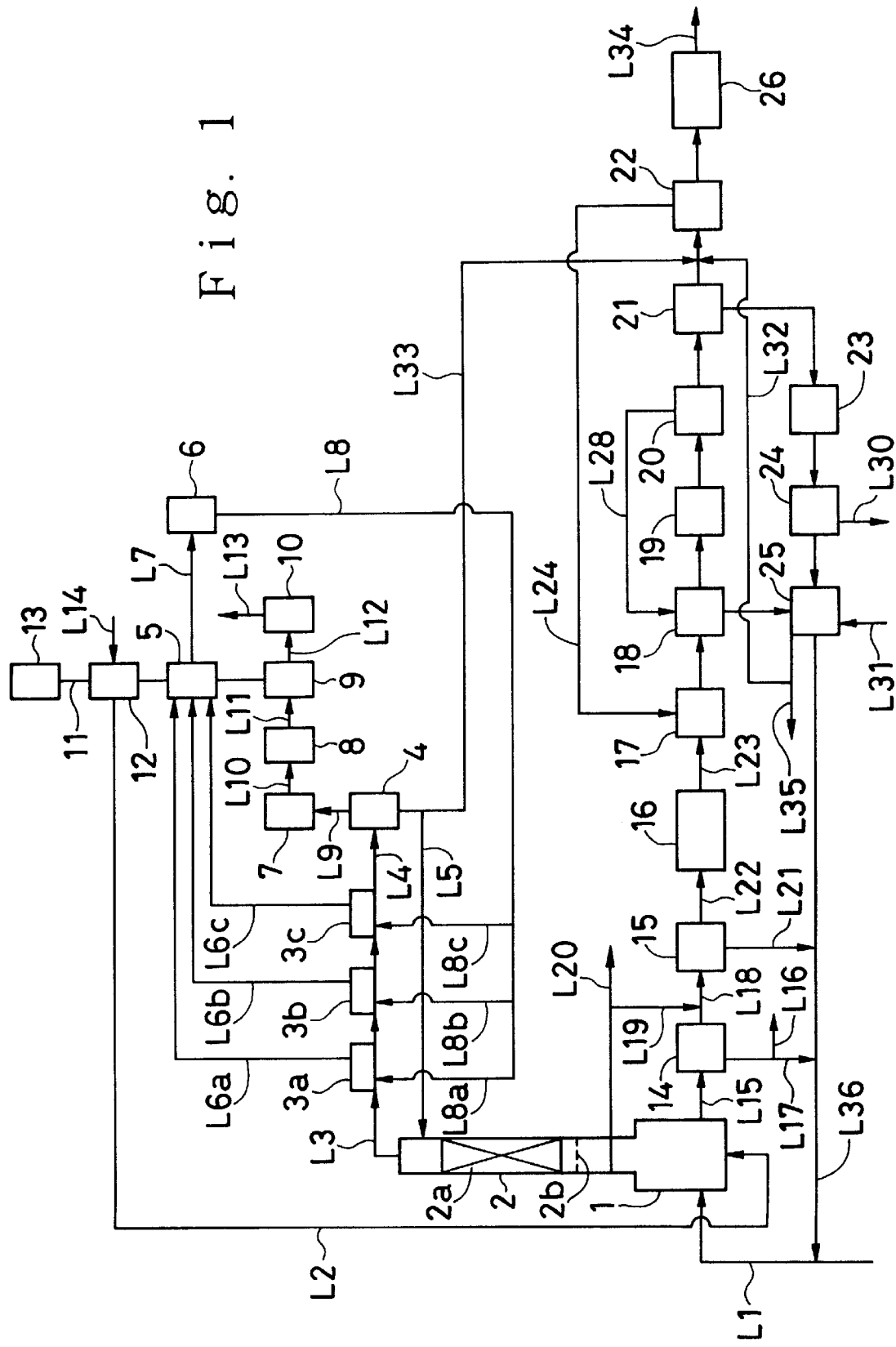
FIG. 1 illustrates an embodiment of the present invention in a flow diagram.

As the starting material to be oxidized for producing the aromatic carboxylic acid according to the present invention, there may be employed aromatic compounds having one or more substituent alkyl groups or partially oxidized alkyl groups (in the following, referred to sometimes simply as oxidation raw material). Such aromatic compounds may either be monocyclic or polycyclic. As the substituent alkyl group, there may be enumerated, for example, those having 1–4 carbon atoms, such as methyl, ethyl, n-propyl and isopropyl. As the substituent partially oxidized alkyl group, there may be enumerated, for example, aldehydo, acyl, carboxyl and hydroxyalkyl.

Concrete examples of the starting aromatic hydrocarbon compounds having alkyl groups, namely alkyl-substituted aromatic hydrocarbons, include di- and polyalkylbenzenes having 2–4 alkyl groups of 1–4 carbon atoms, such as m-diisopropylbenzene, p-diisopropylbenzene, m-cymene, p-cymene, m-xylene, p-xylene, trimethylbenzenes and tetramethylbenzenes; di- and polyalkylnaphthalenes having 2–4 alkyl groups of 1–4 carbon atoms, such as dimethylnaphthalenes, diethylnaphthalenes and diisopropylnaphthalenes; and polyalkylbiphenyls having 2–4 alkyl groups of 1–4 carbon atoms, such as dimethylbiphenyls and the like.

For the aromatic hydrocarbon compounds having partially oxidized alkyl groups, there may be exemplified those in which the alkyl groups of the starting aromatic compounds given above are partially oxidized into, for example, aldehydo, acyl, carboxyl or hydroxyalkyl, as mentioned above. As concrete examples therefor, there may be enumerated 3-methylbenzaldehyde, 4-methylbenzaldehyde, m-toluic acid, p-toluic acid, 3-formylbenzoic acid, 4-formylbezoic acid and 2-methyl-6-formylnaphthalene. They are used either alone or as a mixture of two or more of them.

In the process according to the present invention, a heavy metal compound and a bromine compound are used as the catalyst, wherein the followings are examples of these compounds. Thus, as the heavy metal for the heavy metal compound, there may be enumerated cobalt, manganese, nickel, chromium, zircinium, copper, lead, hafnium and cerium. They can be employed alone or in a combination, with particular preference for a combination of cobalt with manganese.

As the compounds of such heavy metals, there may be exemplified acetate, nitrate, acetylacetonate, naphthenate, stearate and bromide, wherein special preference is given to acetate.

The compound of bromine may include inorganic bromine compounds, such as molecular bromine, hydrogen bromide, sodium bromide, potassium bromide, cobalt bromide and manganese bromide; and organic bromine compounds, such as methyl bromide, methylene bromide, bromoform, benzyl bromide, bromomethyltoluene, dibromoethane, tribromoethane and tetrabromoethane. These bromine compounds may be employed either alone or as a mixture of two or more of them.

For the catalyst according to the present invention constituted of the combination of the heavy metal compound(s) with the bromine compound(s), those in which the molar proportion of the bromine atom relative to the heavy metal atom is in the range from 0.05 to 10 moles, preferably from 0.1 to 2 moles, per one mole of the heavy metal, are preferred. Such catalysts may be incorporated in the reaction mixture usually in an amount in the range from 10–10,000 ppm, preferably from 100 to 5,000 ppm, calculated as the heavy metal concentration in the reaction solvent.

By the process according to the present invention, an aromatic compound as the oxidation raw material is subjected to a liquid phase oxidation in an oxidation reactor in the oxydation step using a liquid reaction solvent comprising a lower aliphatic carboxylic acid with a molecular oxygen-containing gas in the presence of the catalyst mentioned above, in order to obtain the end product of an aromatic carboxylic acid.

As the molecular oxygen-containing gas, there may be enumerated, for example, oxygen gas and atmospheric air, wherein air is favorable for practical use. The molecular oxygen-containing gas is used usually in an excess proportion than that required for oxidizing the oxidation raw material of the aromatic compound into the aromatic carboxylic acid. In case of using air as the molecular oxygen-containing gas, this may favorably be supplied to the reaction system at a rate of 2–20 N m$^3$, preferably 2.5–15 N m$^3$, per one kg of the starting aromatic compound.

As the lower aliphatic carboxylic acid to be used as the reaction solvent, there may be exemplified acetic acid, propionic acid and butyric acid. These lower aliphatic carboxylic acids may be used as the reaction solvent either alone or in a mixture with water. Concrete examples of the reaction solvent include acetic acid, propionic acid, butyric acid and mixtures of them as well as mixtures of them with water. Among them, a mixture of acetic acid with water is preferred, wherein special preference is given to those in which a water content is in the range from 1 to 20 parts by weight, preferably from 5 to 15 parts by weight, per 100 parts by weight of acetic acid.

The temperature of the oxidation reaction may usually be in the range of 100 to 250° C., preferably 150 to 220° C. The pressure in the reaction may be at any level, so long as it permits the reaction mixture to be kept in a liquid state.

By performing the reaction under the condition as above, an aromatic carboxylic acid corresponding to the starting aromatic compound can be obtained. As concrete examples of the aromatic carboxylic acid, there may be enumerated aromatic dicarboxylic acids, such as terephthalic acid, isophthalic acid, 2,6-naphthalene dicarboxylic acid and 4,4'-biphenyl dicarboxylic acid; aromatic tricarboxylic acids, such as trimellitic acid and trimesic acid; and aromatic polycarboxylic acids, such as pyromellitic acid and the like.

It is favorable to apply the process according to the present invention to production of aromatic dicarboxylic acids and of such aromatic carboxylic acids as are insoluble or difficultly soluble in the reaction solvent employed, in particular, to the production of terephthalic acid.

The resulting aromatic carboxylic acid will be deposited in the reaction mixture as crystals to form a slurry, which is drawn out of the oxidation reactor and is subjected to a liquid/solid separation to obtain a crude crystalline product of, such as terephthalic acid.

The so-obtained crude crystalline product contains usually impurities and intermediate products and, therefore, should subsequently be subjected to purification treatment steps comprising re-dissolution of the crude crystals, oxidation treatment, reduction treatment and recrystallization of the end product, such as terephthalic acid, whereby a slurry containing the crystalline end product is obtained. Recovering the crystals from such a slurry, purified end product of, such as terephthalic acid, is obtained.

The process according to the present invention may preferably be performed in the manner, which comprises distilling the oxidation reactor exhaust vapor by making use of the heat generated by the oxidation reaction, returning the components of which boiling points are higher than water to the oxidation reactor from the distillation column, while retaining the lower boiling esters of aliphatic carboxylic acid in the gas from a condenser connected to the oxidation column, recovering the lower boiling esters of the aliphatic carboxylic acid by absorbing them in acetic acid absorbent and recycling this absorbent as such to the oxidation reactor to subject the recovered esters to the oxidation reaction.

In the distillation step, the oxidation reactor exhaust gas is guided into a distillation column (high pressure distillation column) connected to the upper portion of the oxidation reactor and is subjected to distillation under utilization of the heat generated in the oxidation reaction in the reactor, wherein the bottom fraction containing the reaction solvent is returned to the oxidation reactor and the water vapor and non-condensing gases are discharged out of the distillation column as the overhead gas. As the distillation column, there may be employed, for example, one which is arranged independently of the oxidation reactor, as disclosed in Japanese Patent Publication Sho-54-14098 B, or one which is arranged above the oxidation reactor under direct combination therewith, as disclosed in Japanese Patent Application Kokai Hei-6-279353 A. Such distillation column may be designed as a plate tower, while a packed tower type is preferred, wherein it is preferable to arrange such a means as solid material collecting tray for collecting fine solid materials, such as the product crystals, beneath the packing layer.

It may be preferable to incorporate a plurality of distillation columns in series flow so as to effect the distillation in a successive cascade in which the overhead gas from a preceding column is guided to the subsequent column, while refluxing the bottom of subsequent column to the preceding column, wherein each column may favorably be designed so as to permit withdrawal of an intermediate distillate fraction from a middle portion of the column in emergency, in order to prevent the solvent from dilution by flowing down of the water retained in the upper part of the ditillation column.

By performing the distillation in a distillation column as above, the reaction solvent in the oxidation reactor exhaust gas is returned to the oxidation reactor. The returned effluent contains unreacted starting alkyl aromatic compound, the formed aromatic carboxylic acid and the catalyst each in a concentrated state in addition to the reaction solvent, which are concentrated in the bottom part of the column and are returned to the oxidation reactor. Among them, the solid ingredients, such as the crystalline aromatic carboxylic acid and catalyst, as well as the higher boiling ingredients may be concentrated in the lower sections of the column and the lower boiling components, such as the low boiling reaction solvent of aliphatic carboxylic acid and so on, are concentrated in relatively higher portions of the column. These fractions are returned as such to the oxidation reactor.

It may be convenient that the ditillation column is provided at a lower portion thereof with a liquid extraction port for extracting a distillate fraction having a higher concentration of acetic acid in order to use it as the absorbent for absorbing the aliphatic carboxylic acid esters and even as the washing loquor for washing the crystalline product separated by the solid/liquid separation of the slurry withdrawn from the oxidation reactor. Upon an emergent interruption of the oxidation reaction, withdrawal of the distillate out to the outside of the system may serve for prevention of uncontrolled return of the condensate to the oxidation reactor to cause decrease in the concentration of the reactants in the reactor.

In the overhead condensing step, the distillation column overhead gas is cooled in the condenser by a cooling water to cause condensation of water vapor contained in the column overhead gas as condensate which is refluxed to the distillation column while the lower boiling aliphatic carboxylic acid is retained in the gas phase. A part of the cooling water in the cooling shell is vaporized by the heat exchange to generate a steam from which an energy can be recovered. It is preferable to employ a plurality of condensers disposed in a sequence operable to effect sequential condensation of the distillation overhead gas to obtain separate steam fractions having different enthalpies.

By employing a condenser of a kettle type, steam can be obtained without incorporating a separate vessel for steam generation. By controlling the condenser temperature such that the temperature of the exit gas from the condenser is adjusted within a range from 50 to 150° C., the low boiling aliphatic acid esters, such as methyl acetate etc., can be retained in the gas phase, whereby it is made possible to attain effective utilization of the condensed water of the condenser by, for example, using it as the washing water for the product crystals, with simultaneous advantage of attainment of easy waste water treatment upon discharge of the excess condensed water as a spent service water out of the system.

In the burning step, the condenser exit gas is burnt in a burning chamber. Here, if necessary, the condenser exit gas may be heated or, alternatively, it is passed to a catalyst layer after having been, if necessary, enriched with a supplemental fuel, in order to attain burning of substantially entire combustible components in the condenser exit gas. Here, recovery of methyl acetate and recycling thereof to the oxidation reactor may be incorporated, though such recovery may be dispensed with, when such recovery may require a considerable economical expenditure. By the burning, pollutant substances, such as methyl bromide etc., will be decomposed, while causing the temperature of the combustion gas to elevate.

In the energy recovering step, energy is recovered from the steam generated from the cooling water by heat exchange in the condenser and from the combustion gas formed in the burning chamber. By passing the steam and the combustion gas to steam turbine and to gas turbine, respectively, the energy recovery is attained by converting the heat contents of them into rotational mechanical energy using compact energy recovering apparatuses. Energy recovery may be realized using one single gas turbine. When a plurality of condensers arranged in series are employed, steams of different heat content levels generated from different condensers may be guided into corresponding stages of the steam turbine to drive it.

The energy recovered in this manner can be used for compressing the molecular oxygen-containing gas before it is supplied to the oxidation reactor to effect the oxidation efficiently, while the energy can also be used for electric power generation. In practice, the rotary shafts of the steam turbine and the gas turbine are connected directly to build up a single rotary shaft connected to a gas compresor and a power generator, whereby an efficient energy reclamation can be achieved with efficient utilization thereof.

Since the oxidation reaction is an exothermic reaction, such a successively generated heat energy may be reclaimed to promote the reaction efficiently and to operate the entire arrangement in an efficient manner, whereby the running cost of the arrangement can be decreased.

In the present invention, it is preferable to perform absorption of the esters of aliphatic carboxylic acid contained in the condenser exit gas by an absorbent liquor comprising an aliphatic carboxylic acid by bringing the condenser exit gas into contact with the absorbent liquor before it is burnt in the burning chamber, in order to reuse the recovered esters of the aliphatic carboxylic acid in the oxidation reaction. A lower boiling aliphatic carboxylic acid, such as acetic acid, is employed as the reaction solvent. In a conventional technique, the oxidation by-products, such as methyl acetate and the like, are once hydrolysed to recover acetic acid which is recycled to the oxidation reactor. In contrast thereto, in the process according to the present invention, the by-produced methyl acetate etc. can be recovered by absorption in an absorbent liquor comprising an aliphatic carboxylic acid. The spent absorbent liquor containing absorbed therein the by-produced methyl acetate etc. can be returned directly to the oxidation reactor without passing a hydrolysis atep, whereby the reclamation of the by-produced esters is simplified.

The distillation column overhead gas containing water vapor and the lower boiling aliphatic acid esters having boiling points lower than that of water is discharged out of the distillation column and is guided into the condenser. Upon cooling the distillation column overhead gas in the condenser, if the lower boiling aliphatic acid esters are condensed together with water, separation of such esters from the aqueous condensate becomes difficult, so that the waste water treatment is made also difficult. According to the present invention, the low boiling aliphatic carboxylic acid esters can be separated from the aqueous condensate in the condenser by operating the condenser so as to retain the lower boiling aliphatic carboxylic esters in the gas phase which is to be guided out as the condenser exit gas.

The condenser exit gas is then brought into a gas/liquid contact with an absorbent liquor comprising the aliphatic carboxylic acid, in order to separate the aliphatic carboxylic acid esters in the condenser exit gas by absorption in the absorbent liquor. As the absorbent liquor, a distillate extracted from the distillation column, especially that extracted at a portion near the bottom of the distillation column can favborably be used, since such a distillate has a higher content of the aliphatic carboxylic acid, and thus, has a higher ability for absorbing the by-produced aliphatic carboxylic acid esters. The spent absorbent liquor enriched with the absorbed aliphatic carboxylic acid esters is then recycled as such to the oxidation reactor directly to serve for the oxidation reaction. The aliphatic carboxylic acid esters are utilized for the formation of the aromatic carboxylic acid in the oxidation reactor.

When the aliphatic carboxylic acid of the absorbent liquor is contained in the delivery gas from the absorption step, the aliphatic carboxylic acid in the delivery gas is recovered by washing the delivery gas with water and the recovered aliphatic carboxylic acid is recycled to the oxidation reactor. As the water to be used here, the condensed water formed in the condenser can be used. The so-washed gas from the absorption step is forwarded to the catalytic burning chamber to burn it to form a combustion gas to be used for driving the gas turbine to reclaim energy as a mechanical rotational energy.

As described above, in the process according to the present invention, the distillation overhead gas is guided to the condenser for forming, on the gas side, an aqueous condensate which is refluxed to the distillation column and, on the cooling shell side, a steam which is used to drive the steam turbine, wherein the energy recovery is achieved efficiently by the steam turbine and by the gas turbine driven by the combustion gas from the catalytic burning chamber, so that the production of aromatic carboxylic acid can be realized in a highly efficient manner without suffering from any obstructive phenomenon and without occurrence of clogging of the distillation column.

In addition, according to the present invention, the operation of the condenser for condensing the distillation column overhead gas is performed in such a manner that the aliphatic carboxylic acid esters formed as by-products in the oxidation reactor are retained in the gas phase without being condensed in the condenser and is absorbed in the subsequent absorption step using an absorbent liquor comprising the lower boiling aliphatic carboxylic acid, so that the production of the aromatic carboxylic acid can be realized in a highly efficient manner with lower energy consumption under recovery of useful ingredients including the lower boiling aliphatic carboxylic acid esters.

THE BEST MODE FOR EMBODYING THE INVENTION

Now, the concrete operation of the process for the production of aromatic carboxylic acid according to the present invention is described in more detail by way of concrete embodiments for producing terephthalic acid with reference to the Drawings appended.

FIG. 1 shows a block diagram of one embodiment of the process for producing terephthalic acid according to the present invention, in which the oxidation reactor is indicated by the numeral 1, to the top of which is connected directly a distillation column 2 of a packing layer type and the overhead of the distillation column is connected to a plurality of condensers 3a, 3b, 3c . . . of kettle type.

For producing the aromatic carboxylic acid, the starting alkyl aromatic compound, i.e. paraxylene, the reaction solvent, i.e. acetic acid and the catalyst constituted of heavy metal compound(s) and bromine compound(s) are supplied to the oxidation reactor 1 via a line L1, while supplying thereto simultaneously air as the molecular oxygen-containing gas via a line L2, in order to effect a catalytic heterogeneous oxidation of paraxylene in a liquid solvent under a high-pressure and high-temperature condition to produce terephthalic acid. The produced terephthalic acid is deposited as crystals to form a slurry.

The oxidation reactor exhaust gas is guided in the state of high-temperature/high-pressure to a distillation column 2 and passes through a packing layer 2a while establishing a distillation equillibrium therein. The solid matter entrained in the oxidation reactor exhaust gas is removed in the solid matter collection tray 2b and is returned to the oxidation reactor. In the distillation column 2, higher boiling by-products are concentrated and extracted as a distillate fraction at a portion beneath the packing layer 2a, while the lower boiling fraction of acetic acid is concentrated and extracted at a relatively higher level of the packing layer 2a. These fractions are recycled as the bottom fraction to the oxidation reactor 1 together with the separated solid matter.

The overhead gas of the distillation column 2 is passed to the condensers 3a, 3b, 3c successively in series via a line L3, wherein it is subjected to condensation of steam by cooling by a cooling water flowing on the shell side and is then passed to a gas/liquid separator 4 via a line L4 where the condensed water is separated from the gas phase and is partly returned to the distillation column 2 via a line L5. In the condensers 3a, 3b and 3c, the cooling water on the shell side is heated under heat exchange with the heat of the distillation overhead gas, whereby evaporation of the cooling water occurs on the shell side of each condenser to form each a steam. The so-generated steams, of which heat contents are higher successively for preceding condensers, seen in the direction towards the condenser 3a, are guided via lines L6a, L6b and L6c, respectively, to the corresponding stages of a steam turbine 5 to drive the turbine while giving over their heat contents to the turbine as mechanical rotational energy before being collected in a condenser 6 via a line L7 as a condensate which is recycled as the cooling water through a line L8, branching into lines L8a, L8b an dL8c, to the condensers 3a, 3b and 3c.

The exit gas from the gas/liquid separator 4 retains the lower boiling ingredients, such as methyl acetate etc., in a gaseous state by controlling the exit temperature of the condenser 3c at a temperature in the range from 50 to 150° C., preferably in the range from 90 to 120° C., and is guided to a heater 7 via a line L9 for being heated. The heated gas is guided to a burning chamber 8 via a line L10, where it is passed through a combustion catalyst layer to cause burning thereof. The resulting combustion gas is introduced into a gas turbine 9 via a line L11 to cause it to expand therein to drive the turbine, whereby the enthalpy of the combustion gas is reclaimed as a mechanical rotational energy. The discharged gas from the turbine 9 is guided into a waste gas treating apparatus 10 via a line L12, in which it is freed from problematic components, such as bromine compound etc., by an adequate technique, such as adsorption, before being vented out via a line 13.

The steam turbine 5 and the gas turbine 9 constitute together a single energy recovery unit by connecting their rotary shafts directly with each other into a single rotary shaft 11 to which a gas compressor 12 and a power generator 13 are connected as loads. The steam turbine 5 and the gas turbine 9 serve for driving the gas compressor 12 and the electric power generator 13 by making use of the reclaimed rotational energy, on the one hand, to compress the supplying air as the molecular oxygen-containing gas guided from a line L14 and to be supplied to the oxidation reactor 1 via the line 2 for efficient utilization of the energy therein and, on the other hand, to generate an electric power by the generator 13 for utilization of the reclaimed energy as electric power.

On starting the apparatus, the power generator 13 is first operated as a motor by supplying an electric power thereto to drive the gas compressor 12 in order to start the oxidation reaction, while recovering energy using the steam turbine 5 and the gas turbine 9 from the oxidation reactor exhaust gas exhausted on the progress of the oxidation reaction. After the operation of the apparatus has reached to the normal operation, the apparatus is operated under successive recovery of the energy of reaction heat from the exothermic oxidation reaction to utilize it, for example, for operation of pumps and for heating other facilities, in addition to the operation of the compressor 12.

In the course of successive progress of the oxidation reaction, terephthalic acid continues to deposite out of the reaction solution as crystals to form a slurry in the oxidation reactor 1. This slurry is discharged from the reactor via a line L15 and is processed in the solid/liquid separator 14 to separate the crystalline product from the mother liquor. The so-separated mother liquor is discharged in a small portion out of the production system via a line L16 in order to suppress accumulation of impurities and is recycled in the most portion to the oxidation reactor 1 via a line L17 through the line L1. The separated crystalline product is transferred to a second solid/liquid separator 15 through a line L18, while mixing the crystalline product with an aqueous acetic acid side-cut from the distillation column 2 from a line L19 disposed at a lower portion thereof, in order to wash the crystalline product at the solid/liquid separator 15. In order to cope with an accident of contingent cessation of the operation of oxidation reactor 1, a line L20 which usually is kept closed is arranged for permission of withdrawal of a dilute aqueous acetic acid solution from the distillation column out to the outside of the system in order to prevent undesirable dilution of the reaction mixture in the oxidation reactor 1.

The mother liquor separated in the second solid/liquid separator 15 is returned to the oxidation reactor 1 via a line L21, while the crystals are guided into a drier 16 via a line L22 to dry the crystals to obtain a crude terephthalic acid (CTA) product. Here, it is permissible to employ only one solid/liquid separator instead of two separators 14 and 15 and to interpose a washing step between the first and the second separations using an aqueous acetic acid. It is also permitted to cause a pressure change from the high pressure to a lower pressure at an intermediate point between them or at an adequate point around them.

For further purification of the crude terephthalic acid dried in the drier 16, it is transferred from the drier to a mixer 17 via a line L23 and re-slurried there by water recycled through a line L24. The re-slurried crude terephthalic acid is heated in a heat exchanger 18 and is dissolved there by the temperature elevation. The resulting solution is transferred to a reducing reactor 19 charged with solid catalyst of, such as palladium, and is subjected there to a hydrogenation treatment in order to treat the impurities including 4-carboxybenzaldehyde (4-CBA) as the representative one by reducing them.

The so-treated solution is then transferred to a crystallization tank 20, where the solution is subjected to evaporation of water while relieving the pressure, whereby it is cooled and concentrated to cause deposition of pure crystals of terephthalic acid. The thereby produced steam is supplied via a line L28 to the heat exchanger 18 to utilize its heat content as a part of the heat source. The additional heat required for dissolving the crude terephthalic acid in the heat exchanger 18 is supplemented by, for example, a high-pressure steam or a hot oil. The resulting slurry of the deposited crystals of terephthalic acid is forwarded to solid/liquid separators 21, 22 to separate there terephthalic acid crystals from mother liquor.

The mother liquor separated from the crystals in the solid/liquid separator 21 is guided to a cooling vessel 23, where imperities, such as paratoluic acid etc., are caused to precipitate by cooling. The precipitated impurities are separated from the mother liquor in a separator 24 and is guided out of the production system via a line L30. The mother liquor freed from the precipitated impurities and the mother liquor coming from the heat exchanger 18 via a line L28 are guided into an extractor 25 and the so-united mother liquor is subjected to an extraction with paraxylene supplied thereto via a line L31 in order to extract off the remaining unprecipitated impurities from the mother liquor. The mother liquor so-deprived of impurities is sent as washing water to the solid/liquid separator 22 through a line L32 and is used together with the washing water coming from a line L33 to wash the terephthalic acid crystals separated in the solid/liquid separator 21, by re-slurrying them and separating off the washing liquid therefrom in the solid/liquid separator 22.

The separated washing liquid is returned to the mixer 17 as a re-slurrying liquid via the line L24, while the crystals are transferred to a drier 26, from which the dried and purified terephthalic acid (PTA) is taken out via a line L34. The excess amount of water used for the purification in the extractor 25 is discharged out of the system via a line L35. The waste water treatment can easily be attained, since the reaction solvent and by-products have been removed. The spent paraxylene used for the extraction in the extractor 25 is guided to the oxidation reactor 1 via a line L36 and through the line L1.

In the above embodiment, the heat content of the exhaust gas from the oxidation reactor 1 is recovered by the turbine 9 after it has been passed through the condensers 3a, 3b and 3c to condense steam contained in the exhaust gas, so that the energy recovery can be attained under exclusion of obstructive phenimena in the gas turbine due to corrosive substances and scale forming ingredients in the exhaust gas. The cooling water fed to the condensers turns to a steam which can be used for energy recovery by driving the steam turbine 5, so that sufficient energy is recovered from the oxidation reactor exhaust gas. Here, the energy recovery efficiency can be increased by employing a plurality of condensors to effect multistage energy recovery with steams of different heat contents.

When the condensed waters from the condensers 3a, 3b and 3c are refluxed to the distillation column 2, the distillation can be realized efficiently while avoiding stuffing or clogging of the distillation column 2. On an accidental cessation of operation of the production system, the unwanted dilution of the reaction mixture in the oxidation reactor 1 can be prevented by withdrawing the water maintained in the distillation column 2 through the line L20 to thereby the restart of operation of the system can be made easy.

In the above explanations, the procedure may be altered such that the waters from the lines L32 and L33 are introduced into the mixer 17 for effecting water-wash of the crystals in the solid/liquid separator 22. While the solid/liquid separators are employed in a pair, as 14, 15 and 21, 22, such a pair may be replaced with one single apparatus having a mechanism for washing the separated crystals, such as a rotary screen or centrifuge.

Figure 2:
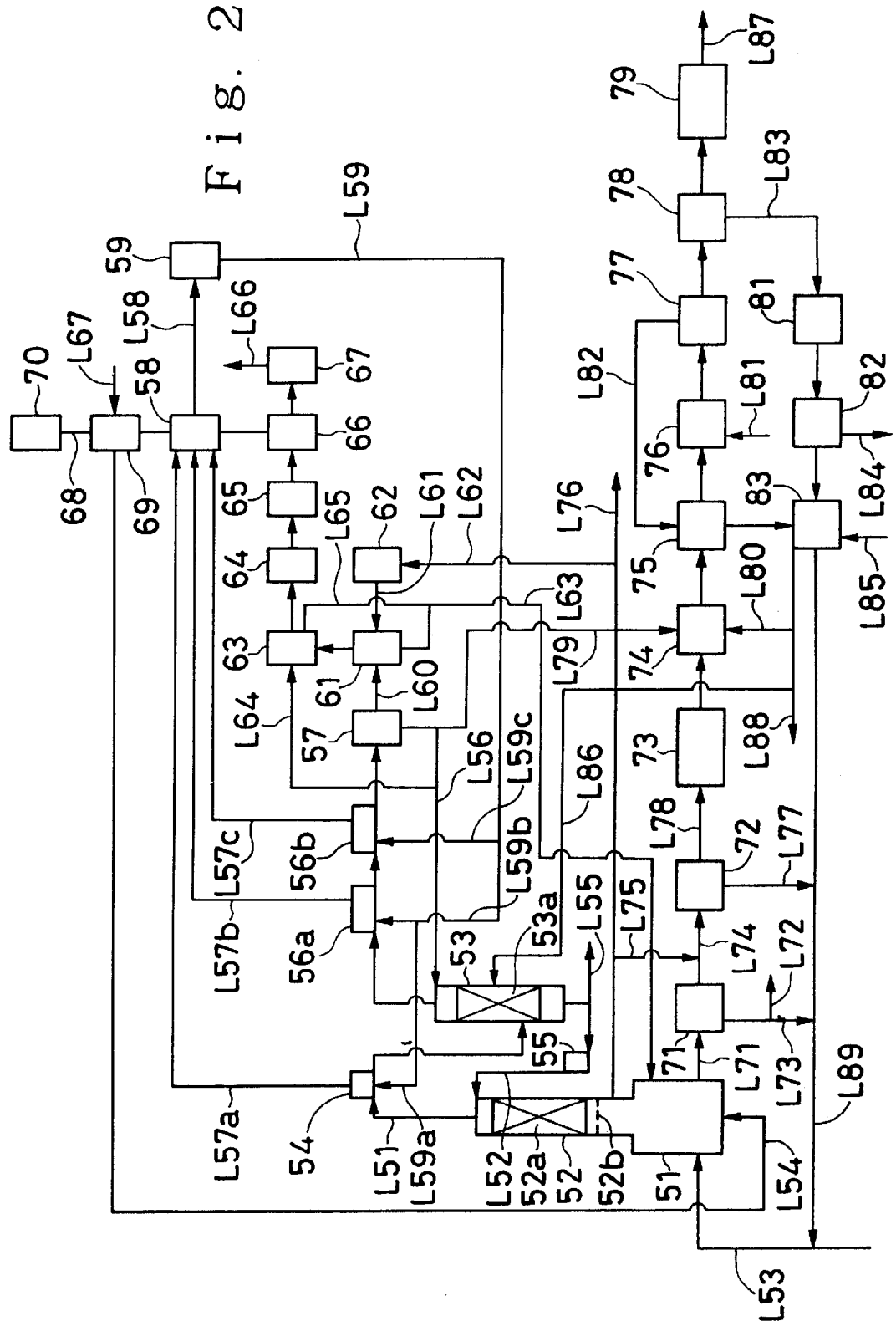
FIG. 2 illustrates another embodiment of the present invention also in a flow diagram.

FIG. 2 is a block diagram showing another embodiment of the process according to the present invention for producing terephthalic acid. In FIG. 2, the oxidation reactor is indicated by a numeral 51 to the top of which is connected directly a first distillation column 52 of a packing layer type and the overhead of this distillation column is connected to a second distillation column 53 via a line L51 provided therein with an intercooler 54 of a kettle type. The bottom of the second distillation column 53 is connected to the top of the first distillation column 52 via a line L52 provided therein with a pump 55.

For producing the aromatic carboxylic acid, the starting alkyl aromatic compound, i.e. paraxylene, the reaction solvent, i.e. acetic acid and the catalyst constituted of heavy metal compound(s) and bromine compound(s) are supplied to the oxidation reactor 51 via a line L53, while supplying thereto simultaneously air as the molecular oxygen-containing gas via a line L54, in order to effect a catalytic heterogeneous oxidation of paraxylene in a liquid solvent under a high-pressure and high-temperature condition to produce terephthalic acid. The produced terephthalic acid is deposited as crystals to form a slurry.

The oxidation reactor exhaust gas is guided in the state of high-temperature/high-pressure to the first distillation column 52 and passes through a packing layer 52a while establishing a distillation equillibrium therein. The solid matter entrained in the oxidation reactor exhaust gas is removed in the solid matter collection tray 52b and is returned to the oxidation reactor. In the first distillation column 52, higher boiling by-products and paraxylene are concentrated and extracted as a distillate fraction at a portion beneath the packing layer 52a, while the lower boiling fraction containing a part of acetic acid is concentrated and extracted at a relatively higher level of the packing layer 52a. These fractions are recycled as the bottom fraction to the oxidation reactor 51 together with the separated solid matter.

The overhead gas from the first distillation column 52 is guided to the tube side of the intercooler 54 via the line L51 and is subjected to cooling by the cooling water in the shell side thereof, whereby a part of the water vapor contained in the overhead gas is condensed while reducing the gas volume and while vaporizing the cooling water in the shell side to generate a steam. The intercooler exit gas deprived of a part of water vapor content is then introduced into the bottom portion of the second distillation column 53 having a packing layer 53a, where the remaining acetic acid is substantially distilled off. The distillate fraction containing acetic acid is recycled via the line L52 by the pump 55 to the first distillation column 52. On an accidental cessation of the productionsystem, the pump 55 is stopped and the reflux liquor is withdrawn through a line L55.

By installing a plurality of distillation columns in this manner, an accidental reflux of a distillate fraction of low concentration and low temperature to the oxidation reactor 51 upon a contingent interruption of the operation of production system can be prevented by withdrawing the reflux liquor from the succeeding distillation column. By the arrangement of an intercooler 54 between the first and the second distillation columns 52 and 53 to recover a part of the heat content of the oxidation exhaust gas and condensation of a part of the steam content thereof with reduction of the gas volume, the diameter of the second distillation column can be reduced. Instead of the intercooler 54, a side reboiler may be installed for heating the overhead gas, whereby, in this case, the height of the second distillation column 53 can be reduced. It is permissible to employ both of them.

On guiding the overhead gas from the second distillation column 53 into condensers 56*a* and 56*b* successively, the overhead gas is cooled by the cooling water flowing on the shell side of these condensers with condensation of its water vapor content and is then subjected to a gas/liquid separation in a gas/liquid separator 57, from which a part of the condensate is refluxed to the second distillation column 53 via a line L56. In the intercooler 54 and the condensers 56*a* amd 56*b*, the cooling water is vaporized by heat exchange with the hot overhead gas to form a steam. The energy levels of the so-formed steams are higher in the direction towards the intercooler 54, with that of the condenser 56*b* being the lowest. These steams are introduced into a steam turbine 58 via each a line L57*a*, L57*b* or L57*c*, respectively, to serve for driving the turbine to thereby deliver their energies to the turbine as mechanical rotational energy, before being collected into a condenser 59 via a line L58. The condensate of the condenser 59 is branched into three delivery flows through lines L59*a*, L59*b* and L59*c* to feed to the intercooler 54, condensers 56*a* and 56*b* as cooling water.

The exit gas from the gas/liquid separater 57 retains the impurities including the aliphatic carboxylyc acid esters, such as methyl acetate etc., in a gaseous state by controlling the exit temperature of the condenser 56*b* at a value in the range from 50 to 150° C., preferably from 90 to 120° C. This gas/liquid separator exit gas is guided into an absorber 61 via a line L60, in which it is brought into gas/liquid contact with an absorbing liquid introduced thereinto from a cooler 62 via a line L61 to absorb methyl acetate in the absorbing liquid. For the absorbing liquid, a distillate fraction having an acetic acid content side-cut from the first distillation column 52 at its bottom via a line L62 and cooled in the cooler 62 may be employed.

The absorbing liquid containing methyl acetate absorbed in the absorber 61 is recycled to the oxidation reactor 51 via a line L63 to serve for the oxidation reaction. The delivery gas from the absorber 61 is guided into a washing apparatus 63 and is washed here with a washing water intyroduced thereinto via a line L64 by a gas/liquid contact therewith to wash out the residual content of acetic acid. The spent washing liquid is recycled to the oxidation reactor via a line L65 and through the line L63 to serve for the oxidation reaction.

The exit gas from the washing apparatus 63 is guided into a heating vessel 64 and is heated here. The heated gas is guided then into a burning chamber 65, where it is passed through a combustion catalyst layer to cause burning thereof. The resulting combustion gas is introduced into a gas turbine 66 to cause it to expand therein to drive the turbine, whereby the enthalpy of the combustion gas is reclaimed as a mechanical rotational energy. The discharge gas from the gas turbine 66 is guided into a waste gas treating apparatus 67, in which it is freed from problematic components, such as bromine compound etc., by an adequate technique, such as adsorption, before being vented out via a line L66.

The steam turbine 58 and the gas turbine 66 constitute together a single energy recovery unit by connecting their rotary shafts directly with each other into a single rotary shaft 68 to which a gas compressor 69 and a power generator 70 are connected as loads. The steam turbine 58 and the gas turbine 66 serve for driving the gas compressor 69 and the electric power generator 70 by making use of the reclaimed rotational energy, on the one hand, to compress the supplying air as the molecular oxygen-containing gas guided from a line L67 and to be supplied to the oxidation reactor 51 via the line L54 for efficient utilization of the energy therein and, on the other hand, to generate an electric power by the generator 70 for utilization of the reclaimed energy as electric power.

On starting the apparatus, the power generator 70 is first caused to act as a motor by supplying an electric power thereto to drive the gas compressor 69, in order to start the oxidation reaction, while recovering energy using the steam turbine 58 and the gas turbine 66 from the oxidation reactor exhaust gas exhausted on the progress of the oxidation reaction. After the operation of the apparatus has reached the normal operation, the apparatus is operated under successive recovery of the energy of reaction heat from the exothermic oxidation reaction to utilize it, for example, as powers for the pump 55 and others and for heating other facilities, in addition to the operation of the gas compressor 69.

In the course of successive progress of the oxidation reaction, the formation of terephthalic acid continues to deposite out of the reaction solution as crystals to form a slurry in the oxidation reactor 51. This slurry is discharged from the reactor via a line L71 and is processed in the solid/liquid separator 71 to separate the crystalline product from the mother liquor. The so-separated mother liquor is discharged in a small portion out of the production system via a line L72 in order to suppress accumulation of impurities and is recycled in the most portion to the oxidation reactor 51 via a line L73 through the line L53. The separated crystalline product is transferred to a second solid/liquid separator 72 through a line L74, while mixing the crystalline product with an aqueous acetic acid extracted from the first distillation column 52 from a line L75 disposed at a lower portion thereof, in order to effect washing of the crystalline product at the solid/liquid separator 72. In order to cope with an accident of contingent cessation of the operation of the production system, a line L76 which usually is kept closed is arranged for permission of withdrawal of a dilute aqueous acetic acid solution from the distillation column 52 out to the outside of the system in order to prevent undesirable dilution of the reaction mixture in the oxidation reactor 51.

The mother liquor separated in the solid/liquid separator 72 is returned to the oxidation reactor 51 via a line L77, while the crystals are guided into a drier 73 via a line L78 to dry the crystals to obtain a crude terephthalic acid (CTA) product. Here, it is permissible to employ only one solid/liquid separator instead of two separators 71 and 72 and to interpose a washing step between the first and the second separations using an aqueous acetic acid. It is also permitted to cause a pressure change from the high pressure to a lower pressure at an intermediate point between them or at an adequate point around them.

For further purification of the crude terephthalic acid dried in the drier 73, it is transferred from the drier to a mixer 74 and re-slurried there by the condensate supplied via a line L79 and water recycled through a line L80. The re-slurried crude terephthalic acid is heated in a heat exchanger 75 and is dissolved there by the temperature elevation. The resulting solution is transferred to a reducing reactor 76 charged with solid catalyst of, such as palladium, and is subjected there to a hydrogenation treatment by hydrogen supplied thereto via line L81 in order to treat the impurities including 4-carboxybenzaldehyde (4-CBA) as the representative one by reducing them.

The so-treated solution is then transferred to a crystallization drum 77, where the solution is subjected to evaporation of water while relieving the pressure, whereby it is cooled and concentrated to cause crystallization of terephthalic acid as pure crystals. The thereby produced steam is supplied via a line L82 to the heat exchanger 75 to utilize its heat content as a part of the heat source. The additional heat required for dissolving the crude terephthalic acid in the heat exchanger 75 is supplemented by, for example, a high-pressure steam or a hot oil. The resulting slurry of the deposited crystals of terephthalic acid is forwardedto solid/liquid separators 78 to separate there terephthalic acid crystals from the mother liquor. While there is used here a single solid/liquid separator 78, it is possible to use a plurality of solid/liquid separators, such as those 71 and 72 with incorporation of a washing step therebetween.

The mother liquor separated from the crystals in the solid/liquid separator 78 is guided to a cooling vessel 81, where imperities, such as paratoluic acid etc., are caused to precipitate by cooling. The precipitated impurities are separated from the mother liquor in a separator 82 and is guided out of the production system via a line L84. The mother liquor freed from the deposited impurities and the mother liquor coming from the heat exchanger 75 via a line L82 are guided into an extractor 83 and the so-united mother liquor is subjected to an extraction with paraxylene supplied thereto via a line L85 in order to extract off the remaining unprecipitated impurities from the mother liquor. A part of the mother liquor so-deprived of imperities is sent as the slurrying water and the other part thereof is sent to the second distillation column 53 at its middle portion via a line L86.

The crystals separated in the solid/liquid separator 78 are dried in a drier 79 and is withdrawn via a line L87 as a purified terephthalic acid product (PTA). The water from extractor 83 is discharged out of the system as excess water via a line L88. Here, the waste water treament can easily be performed, since the excess water has been freed from the reaction solvent, by-products and so on. The spent paraxylene used for the extraction in the extractor 83 is guided into the oxidation reactor 51 via a line L89 and through the line L53.

In the above embodiment, the condensation of the overhead gas from the distillation column in the condensers 56a and 56b is performed so as to maintain the aliphatic carboxylic acid ester by-produceud in the oxidation reaction, namely, methyl acetate, in the gas phase, and so as to absorb the aliphatic carboxylic acid ester in the absorption step by an absorbing liquid containing acetic acid in the absorber 61 before recycling to the oxidation reactor 51, so that an efficient production of the aromatic carboxylic acid (terephthalic acid) can be attained with lower energy consumption under recovery of methyl acetate.

By washing the delivery gas from the absorber 61 in a washing apparatus 63 to absorb acetic acid therein and to recycling the spent washing liquid to the oxidation reactor, a more efficient production can be attaind.

By installing two distillation columns, it is made possible to withdraw a reflux liquor from the distillation column at its middle portion out to the outside of the system upon an emergency, whereby an undesirable reduction in the concentration and in the temperature of the oxidation reactor upon an accidental cessation of the operation of the production system can be prevented and thereby a restart of the system can be realized at once when the accidental condition is relieved. When it is made possible to extract a distillate fraction from the first distillation column 52 at its bottom portion, the above effect may further be increased.

When the water vapor content in the overhead gas from the second distillation column 53 is condensed in the condensers 56a and 56b before the gas is utilized for energy recovery by the gas turbine 66, the energy recovery can be realized under exclusion of obstructive phenomena in the gas turbine, such as corrosion and scale formation due to the corrosive or scale-forming substances contained in the gas. The cooling water fed to the condensers turns to steam which can be used for energy recovery by driving the steam turbine 58, so that sufficient energy is recovered from the oxidation reactor exhaust gas. Here, the energy recovery efficiency can be increased by employing a plurality of condensers to effect multistage energy recovery with steams of different heat contents. Here, the energy recovery efficiency can be increased by performing the condensation in a plurality of condensers so as to produce steams of different energy levels. By recycling the condensates from the condensers 56a and 56b to the distillation column 53, stuffing or clogging of the distillation column 53 is prevented and the distillation can be attained efficiently.

In the above explanations, it may be altered that the washing water from the lines L79 and L80 is introduced into the solid/liquid separator 78. The solid/liquid separators 71 and 72 or 78 may be either a single unit or composed of a plurality of units. When a washing mechanism is provided, such as a rotary screen and centrifuge, a single apparatus may be employed therefor.

What is claimed is:

1. A process for producing aromatic carboxylic acid by a liquid phase oxidation of an alkyl aromatic compound with a molecular oxygen-containing gas under a high temperature/high pressure condition in an oxidation reactor, comprising an oxidation step in which the alkyl aromatic compound is oxidized in a liquid reaction solvent comprising an aliphatic carboxylic acid with the molecular oxygen-containing gas in the oxidation reactor in the presence of an oxidation catalyst to form an aromatic carboxylic acid, a distillation step in which the exhaust gas from the oxidation reactor is guided to a distillation column to subject it to distillation therein and liquid fractions formed therein containing the reaction solvent are returned to the oxdation reactor, a condensing step in which the distillation column overhead gas is cooled in a condenser so as to form a condensate which is returnd to the distillation column and to generate a steam in the condenser, a burning step in which the condenser exit gas is burnt in a burning chamber and an energy recovering step in which energy is recovered from the heat contents of the steam generated in the condenser and of the combustion gas formed in the burning chamber.

2. The process according to claim 1, comprising further an absorption step in which low boiling esters of the aliphatic carboxylic acid are retained in the gas phase in the condensing step and the condenser exit gas is brought into contact with an absorbing liquid containing an aliphatic carboxylic acid to absorb the aliphatic carboxylic acid esters, whereupon the absorbing liquid which contains the absorbed aliphatic carboxylic acid esters is supplied to the oxidation reactor, while the delivery gas from the absorption step is burnt in the burning chamber.

3. The process according to claim 1, comprising further a gas washing step in which the absorption step delivery gas is brought into contact with a washing water to absorb the aliphatic carboxylic acid contained therein.

4. The process according to claim 1, in which the temperature of the condenser exit gas is maintained within the range from 50 to 150° C. so as to retain methyl acetate within the exit gas.

5. The process according to claim 1, in which energy recovery is effected by means of a steam turbine and a gas turbine.

6. The process according to claim 1, in which the molecular oxygen-containing gas is supplied to the oxidation reactor under compression by using the recovered energy.

7. The process according to claim 1, in which liquid extraction ports are provided on the distillation column.

8. The process according to claim 1, in which a distillate is extracted from the distillation column at a lower portion thereof and this distillate is used as the absorbing liquid.

9. The process according to claim 1, in which the distillation column is constructed so as to permit withdrawal of the distillate of the lower portion of the column out to the system outside in emergency.

10. The process according to claim 1, in which the condensation step is performed using a plurality of condensers in sequence.

11. The process according to claim 1, in which the condenser is a kettle type.

* * * * *